US011189371B2

(12) United States Patent
Spiro et al.

(10) Patent No.: US 11,189,371 B2
(45) Date of Patent: Nov. 30, 2021

(54) SYSTEMS AND METHODS FOR ADJUSTING MEDICAL TREATMENT TO REDUCE LIKELIHOOD OF PRESCRIPTION CASCADE

(71) Applicant: International Business Machines Corporation, Armonk, NY (US)

(72) Inventors: Adam Spiro, Tel-Aviv (IL); Chen Yanover, Zichron Yaakov (IL)

(73) Assignee: International Business Machines Corporation, Armonk, NY (US)

( * ) Notice: Subject to any disclaimer, the term of this patent is extended or adjusted under 35 U.S.C. 154(b) by 118 days.

(21) Appl. No.: 16/398,285

(22) Filed: Apr. 30, 2019

(65) Prior Publication Data

US 2020/0350047 A1 Nov. 5, 2020

(51) Int. Cl.
*G16H 20/10* (2018.01)
*G16H 50/30* (2018.01)
*G16H 10/60* (2018.01)

(52) U.S. Cl.
CPC ............. *G16H 20/10* (2018.01); *G16H 10/60* (2018.01); *G16H 50/30* (2018.01)

(58) Field of Classification Search
CPC ......... G16H 10/60; G16H 20/10; G16H 50/30
USPC .......................................................... 705/3
See application file for complete search history.

(56) References Cited

U.S. PATENT DOCUMENTS

| 2013/0046554 | A1 | 2/2013 | Williams et al. | |
| 2013/0179375 | A1* | 7/2013 | Tatonetti | G06N 20/00 706/12 |
| 2016/0012195 | A1 | 1/2016 | Lee et al. | |
| 2016/0292366 | A1* | 10/2016 | Reiche | G16H 20/10 |
| 2019/0303368 | A1* | 10/2019 | Liu | G06F 16/2465 |
| 2019/0333636 | A1* | 10/2019 | Bennett | G16H 20/00 |
| 2020/0245925 | A1* | 8/2020 | Inwald | G16H 50/20 |

(Continued)

OTHER PUBLICATIONS

Sutherland, Jeffrey J et al. "Co-prescription trends in a large cohort of subjects predict substantial drug-drug interactions." PloS one vol. 10,3 e0118991. Mar. 4, 2015, doi:10.1371/journal.pone.0118991 (Year: 2015).*

(Continued)

*Primary Examiner* — Christopher L Gilligan
*Assistant Examiner* — Bennett Stephen Erickson
(74) *Attorney, Agent, or Firm* — Barry D. Blount (57) ABSTRACT

There is provided a method for generating instructions for adjusting a medical treatment of a patient, comprising: detecting an indication of a new symptom appearing in a patient being treated with medications for medical condition (s), computing a value indicative of risk of the new symptom being an adverse drug reaction (ADR) of one or a combination of the medications, detecting an indication of another new medication for treating the patient, computing likelihood of PC when the new medication is for treating the new symptom and the value is according to a requirement, generating a request for substitute medication(s) for the one or combination of medications when likelihood of PC is detected, and generating instructions for adjusting treatment of the patient by substituting the one or combination of medications with the substitute medication(s), and for terminating administration of the new medication or avoiding administration of the new medication.

20 Claims, 4 Drawing Sheets

(56) References Cited

U.S. PATENT DOCUMENTS

2020/0273578 A1* 8/2020 Kutzko .................. G16H 50/30

OTHER PUBLICATIONS

Ponte ML, Wachs L, Wachs A, Serra HA. Prescribing cascade. A proposed new way to evaluate it. Medicina (B Aires). 2017;77(1):13-16. English. PMID: 28140305. (Year: 2017).*

J. Reps, J. M. Garibaldi, U. Aickelin, D. Soria, J. E. Gibson and R. B. Hubbard, "Comparing data-mining algorithms developed for longitudinal observational databases," 2012 12th UK Workshop on Computational Intelligence (UKCI), Edinburgh, UK, 2012, pp. 1-8, doi: 10.1109/UKCI.2012.6335771. (Year: 2012).*

Niedrig et al. Improving hospital drug safety—identification of medication errors and subsequent development, implementation and outcome evaluation of alert algorithms for their targeted prevention. Zurich Open Repository and Archive, University of Zurich, Main Library, Strickhofstrasse 39, CH-8057 Zurich www.zora.uzh.ch. 2016. pp. 1-158.

Rochon et al. Optimising drug treatment for elderly people: the prescribing cascade, BMJ, vol. 315, Oct. 25, 1997, p. 315:1096-9.

Kalisch et al. The prescribing cascade, Australian Prescriber, vol. 34, No. 6, 2011;34, pp. 162-166.

Ponte et al, Prescribing Cascade. A Proposed New Way to Evaluate It, Medicina (Buenos Aires) 2017, 77: 13-16, ISSN 1669-9106.

* cited by examiner

FIG. 4 ystems and Methods for Adjusting Medical Treatment to Reduce Likelihood of Prescription Cascade

BACKGROUND

The present invention, in some embodiments thereof, relates to systems and methods for treatment of a patient and, more specifically, but not exclusively, to systems and methods for reducing likelihood of a prescription cascade.

Prescription Cascade (PC) is the condition of prescribing additional medications to treat adverse drug reactions (ADRs) of an existing drug, which in turn might trigger new ADRs that may cause the prescription of additional drugs.

SUMMARY

According to a first aspect, a computer implemented method for generating instructions for adjusting a medical treatment of a patient for reducing likelihood of a prescription cascade (PC), comprises: detecting an indication of a new symptom appearing in a patient being treated with a plurality of medications for at least one medical condition, computing a value indicative of risk of the new symptom being an adverse drug reaction (ADR) of one or a combination of the plurality of medications, detecting an indication of another new medication for treating the patient, computing likelihood of PC when the new medication is for treating the new symptom and the value is according to a requirement, generating a request for at least one substitute medication for the one or combination of the plurality of medications when likelihood of PC is detected, and generating instructions for adjusting treatment of the patient by substituting the one or combination of the plurality of medications with the at least one substitute medication, and for terminating administration of the new medication or avoiding administration of the new medication.

According to a second aspect, a system for generating instructions for adjusting a medical treatment of a patient for reducing likelihood of a prescription cascade (PC), comprises: at least one hardware processor executing a code for: detecting an indication of a new symptom appearing in a patient being treated with a plurality of medications for at least one medical condition, computing a value indicative of risk of the new symptom being an adverse drug reaction (ADR) of one or a combination of the plurality of medications, detecting an indication of another new medication for treating the patient, computing likelihood of PC when the new medication is for treating the new symptom and the value is according to a requirement, generating a request for at least one substitute medication for the one or combination of the plurality of medications when likelihood of PC is detected, and generating instructions for adjusting treatment of the patient by substituting the one or combination of the plurality of medications with the at least one substitute medication, and for terminating administration of the new medication or avoiding administration of the new medication.

According to a third aspect, a computer program product for generating instructions for adjusting a medical treatment of a patient for reducing likelihood of a prescription cascade (PC), comprises: a non-transitory memory storing thereon code for execution by at least one hardware process, the code including instructions for: detecting an indication of a new symptom appearing in a patient being treated with a plurality of medications for at least one medical condition, computing a value indicative of risk of the new symptom being an adverse drug reaction (ADR) of one or a combination of the plurality of medications, detecting an indication of another new medication for treating the patient, computing likelihood of PC when the new medication is for treating the new symptom and the value is according to a requirement, generating a request for at least one substitute medication for the one or combination of the plurality of medications when likelihood of PC is detected, and generating instructions for adjusting treatment of the patient by substituting the one or combination of the plurality of medications with the at least one substitute medication, and for terminating administration of the another medication or avoiding administration of new medication.

In a further implementation of the first, second, and third aspect, further comprising, in response to the request, automatically selecting at least one substitute medication according to a computed risk of developing the new symptom in response to treatment with the at least one substitute medication not being according to the requirement.

In a further implementation of the first, second, and third aspect, the indication of the new symptom is detected by an analysis of an electronic health record (EHR) of the patient for determining when a new symptom temporally appears after administration of the one or combination of medications.

In a further implementation of the first, second, and third aspect, the requirement comprises the value indicative of risk of the new symptom being ADR in comparison to a computed value indicative of likelihood of risk of the new symptom appearing when the one or combination of the plurality of medications are not administered.

In a further implementation of the first, second, and third aspect, likelihood of PC is generated when the value indicative of risk of the new symptom being the ADR of one or the combination of the plurality of medications is statistically significantly greater than the computed value indicative of likelihood of risk of the new symptom appearing when the one or combination of the plurality of medications are not administered.

In a further implementation of the first, second, and third aspect, the patient is associated with a plurality of medical parameters, and the value indicative of risk is computed based on data of a population of a plurality of sample individuals correlated with the plurality of medical parameters.

In a further implementation of the first, second, and third aspect, the plurality of medical parameters are selected from the group consisting of: historical and existing patient medical conditions, patient demographics, and age of onset of the medical conditions.

In a further implementation of the first, second, and third aspect, the indication of the new medication is detected when the new medication comprises an existing medication currently being administered to the patient starting temporally after appearance of the new symptom.

In a further implementation of the first, second, and third aspect, the indication of the new medication is detected when the new medication is instructed for future administration.

In a further implementation of the first, second, and third aspect, values indicative of risk that do not meet the requirement are indicative of at least one of: a new medical condition, or progression of an existing medical condition.

In a further implementation of the first, second, and third aspect, the value indicative of risk of the new symptom being an ADR is computed according to data extracted from a structured dataset storing mappings between medications, symptoms, and medical conditions.

In a further implementation of the first, second, and third aspect, further comprising: creating the structured dataset from data extracted from a plurality of datasets, by computing at least one member of the group consisting of: (i) a probability of a certain symptom to appear following treatment with one or a combination of certain medications, (ii) a probability that a certain symptom appears when one or a combination of certain medications are not being administered, (iii) one or a combination of certain drugs having documented evidence for treatment of a certain symptom, (iv) at least one symptom associated with a certain medical condition, (v) one or a combination of certain drugs having documented evidence for treatment of a certain medical condition.

In a further implementation of the first, second, and third aspect, further comprising, in response to the request, automatically analyzing the structured dataset for selecting at least one substitute medication according to a computed risk of developing the new symptom in response to treatment with at least one substitute medication not being according to the requirement.

In a further implementation of the first, second, and third aspect, the plurality of datasets include unstructured data including research publications and case reports.

In a further implementation of the first, second, and third aspect, the new symptom is defined according to a coding standard of symptoms.

In a further implementation of the first, second, and third aspect, further comprising generating a recommendation for an electronic based prescription for the patient based on the generated instructions, wherein the one or combination of the plurality of medications are substituted with at least one substitute medication and wherein the recommendation includes instructions to at least one of terminate and avoid administration of the new medication.

In a further implementation of the first, second, and third aspect, a number of the plurality of medication is at least 5.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

The present invention, in some embodiments thereof, relates to systems and methods for treatment of a patient and, more specifically, but not exclusively, to systems and methods for reducing likelihood of a prescription cascade.

In at least some implementations, the term prescription cascade relates to the case of prescription of medication(s) for treating symptoms caused by other previously prescribed medications.

As used herein, the terms medication and drug are interchangeable.

As used herein, the term medical condition and disease and symptom are sometimes interchangeable.

An aspect of some embodiments of the present invention relates to systems, methods, an apparatus, and/or code instructions (i.e., stored on a data storage device executable by hardware processor(s)) for computing a likelihood of a prescription cascade (PC), and optionally generating instructions for adjusting the medical treatment of the patient to reduce or avoid the PC. An indication of a new symptom appearing in a patient is detected. The patient is being treated with multiple medications for one or more medical condition. A value indicative of risk of the new symptom being an adverse drug reaction (ADR) of one or a combination of the medications, is computed. An indication of another new and/or existing medication for treating the patient is detected. The other new and/or existing medication is different than the one or combination of medications which are associated with risk of ADR for the new symptom. The other new and/or existing medication has been, or is scheduled for, administration after the new symptom has appeared. Likelihood of PC is determined when the new and/or existing medication is for treating the new symptom and the value indicative or risk of the new symptom being ADR is according to a requirement (e.g., risk of ADR is high or significant). An indication of likelihood of PC may be generated, for example, presented on a screen of a user.

Optionally, a request for one or more substitute medications for the one or combination of medications associated with risk of ADR is generated when likelihood of PC is detected. The substitute medication is for treating the same medical condition that the one or combination of medications that are associated with ADR are treating. The substitute medication(s) are selected according to a computed risk of developing the new symptom, where the risk does not meet the requirement (e.g., risk of ADR is low).

Optionally, the substitute medications are manually provided by a user, for example, selected from a list. Alternatively or additionally, the substitute medications are automatically selected (and/or presented as possible options to a user) by code, for example, a computer program, an application, and/or via a software interface.

Optionally, instructions for adjusting treatment of the patient are automatically generated. The instructions may be, for example presented on a display as a recommendation for a user, and/or automatically implemented, for example, by generating a new prescription for the patient. The treatment of the patient is adjusted by substituting the one or combination of the medications associated with risk of ADR with the at least one substitute medication, and administration of the other new and/or existing medication for treatment of the new symptom is terminated and/or not administered.

Optionally, the requirement (which is used to determine whether the risk of the new symptom is ADR) is a comparison of the computed value indicative of risk of the new symptom being ADR in comparison to a computed value indicative of likelihood of the new symptom appearing when one or combination of the medications are not administered, for example, a statistically significant difference.

Optionally, the value indicative of risk of the new symptom being ADR and/or the value indicative of likelihood of the new symptom appearing when one or combination of the medications are not administered, and/or whether the other new and/or existing medication(s) is for treatment of the symptom, are extracted from a structured dataset storing mappings between medications, symptoms, and medical conditions, optionally according to patient parameters (e.g., demographics, co-morbidities, age of onset of medical condition). The structured dataset may be created from unstructured data, for example, research publications and/or case reports.

At least some implementations of the systems, methods, apparatus, and/or code instructions described herein address the medical problem of a prescription cascade. At least some implementations of the systems, methods, apparatus, and/or code instructions described herein improve treatment of a patient. The medical problem of a PC is solved, and/or treatment of the patient is improved, by at least some implementations of the systems, methods, apparatus, and/or code instructions described herein, that detect likelihood of PC when a value indicative of risk of a new symptom in a patient is according to a requirement denoting that the new symptom is an ADR of one or a combination of medications being used to treat the patient, and when another new and/or existing medication (administered after the new symptom has appeared) is for treating the new symptom. When likelihood of PC is high (e.g., above a threshold) or significant (e.g. statistically significant according to a threshold), the patient's treatment is adjusted by substituting the one or combination of medications that likely cause the ADR with other medication(s) unlikely to cause the ADR, and terminating and/or preventing additional administration of the new and/or existing medication for treating the new symptom. At least some implementations of the systems, methods, apparatus, and/or code instructions described herein remove or reduce the new symptom (by substitution of medication(s) that caused the new symptom), and prevent administration of additional medications (for treatment of the new symptom ADR).

At least some implementations of the systems, methods, apparatus, and/or code instructions described herein improve treatment of a patient by preventing or reducing risk of medications being prescribed as part of a prescription cascade.

Figure 1:
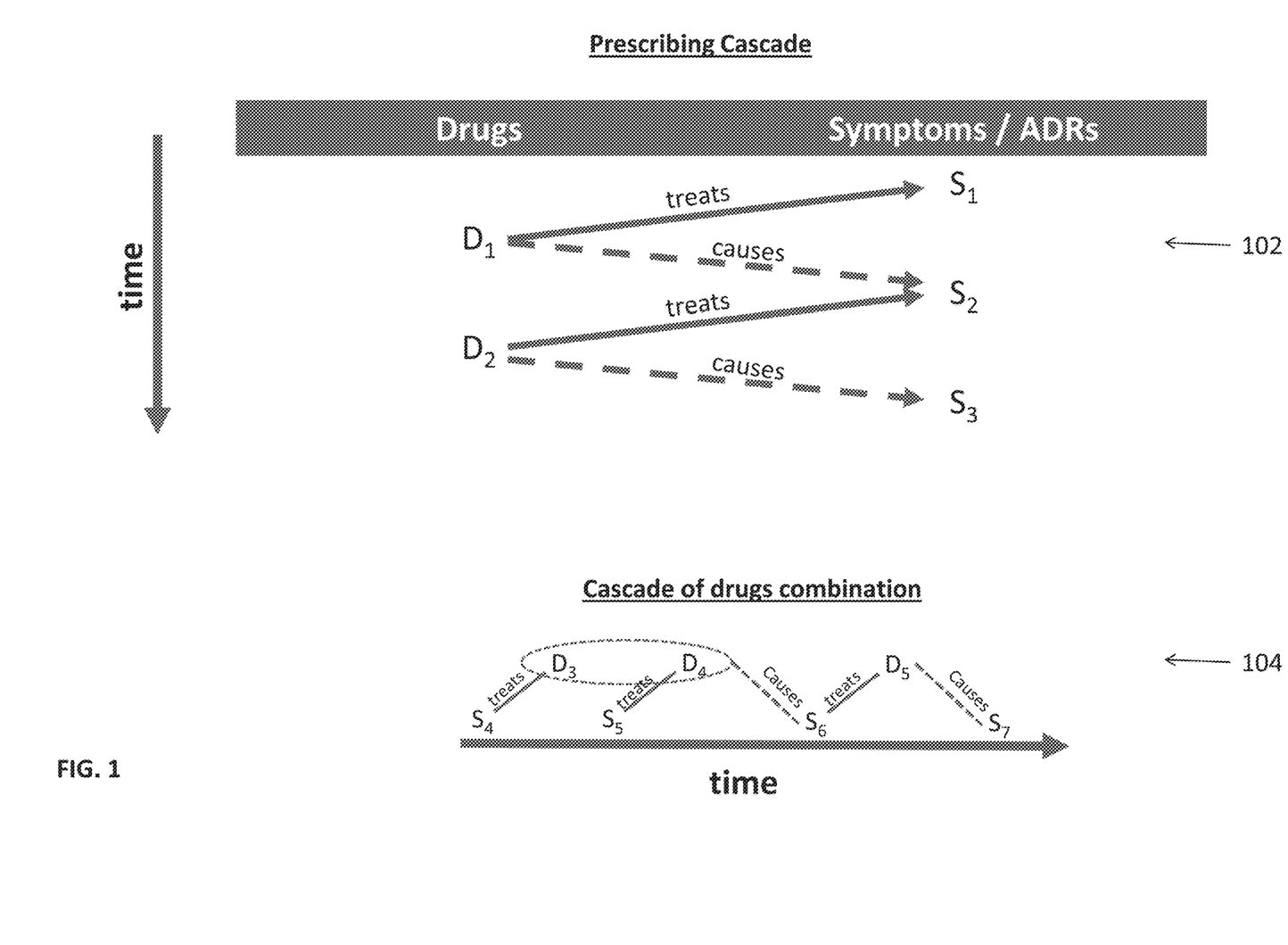
FIG. 1 is a schematic depicting a prescription cascade, in order to help understand the technical problem addressed by at least some embodiments of the present invention.

Reference is now made to FIG. 1, which is a schematic depicting a prescription cascade, in order to help understand the technical problem addressed by at least some embodiments of the present invention. A schematic 102 depicts a patient who suffers from an initial symptom and/or medical condition, denoted $S_1$. In order to treat $S_1$, the physician prescribes a medication drug denoted $D_1$. Another symptom denoted $S_2$ is a side-effect caused by $D_1$. The physician, believing that $S_2$ is a new symptom, a new medical condition, and/or progression of an existing medical condition, prescribes $D_2$ for treatment of $S_2$. The physician in prescribing $D_2$ fails to recognize that $S_2$ is actually a side-effect caused by $D_1$. The prescription of the additional drugs can be due to misidentification of existing ADR as symptoms of a new condition or the necessity to keep taking previously prescribed drugs due to lack of better alternatives. The PC may continue, for example, by appearance of a new symptom denoted $S_3$ which is a side-effect of medication $D_2$, which may trigger yet a third medication for treatment thereof.

At least some implementations of the systems, methods, apparatus, and/or code instructions described herein compute likelihood of PC when $D_2$ is identified as treating $S_2$, and when $S_2$ is likely an ADR caused by $D_1$. The treatment of the patient may be adjusted by substituting $D_1$ with another medication that is unlikely to cause $S_2$ as an ADR, and by stopping or preventing administration of $D_2$.

Schematic 104 depicts the case of a combination of medications participating in a PC. A patient suffers from two symptoms and/or two medical conditions, respectively denoted $S_4$ and $S_5$. Two medications respectively denoted $D_3$ and $D_4$ are prescribed to treat $S_4$ and $S_5$. The combination of $D_3$ and $D_4$ causes a new side effect, a symptom denoted $S_6$. The physician, believing that $S_6$ is a new symptom, a new medical condition, and/or progression of an existing medical condition, prescribes $D_5$ for treatment of $S_6$. The physician in prescribing $D_5$ fails to recognize that $S_6$ is actually a side-effect caused by the combination of $D_3$ and $D_4$. The PC continues by appearance of a new symptom denoted $S_7$ which is a side-effect of medication $D_5$, which may trigger yet a fourth medication for treatment thereof.

At least some implementations of the systems, methods, apparatus, and/or code instructions described herein identify likelihood of PC when $D_5$ is identified as treating $S_6$, and when $S_6$ is likely an ADR caused by the combination of $D_3$ and $D_4$. The treatment of the patient may be adjusted by substituting $D_3$ and $D_4$ with another medication or combination of medications that is unlikely to cause $S_6$ as an ADR, and by stopping or preventing administration of $D_5$, which has the further benefit of preventing $S_7$.

At least some implementations of the systems, methods, apparatus, and/or code instructions described herein provide improvements over known methods for addressing the problem of PC. For example, Known methods based on prevention of PC are based on increasing awareness of the physician and/or patients to the risk of PC. For example, Rochon P A, Gurwitz J H, *Optimising drug treatment for elderly people: the prescribing cascade, BMJ.* 1997 Oct. 25; 315(7115): 1096-9 states "To prevent the prescribing cascade, doctors should always consider any new signs and symptoms as a possible consequence of current drug treatment. Before any new drug treatment is started, the need for the drug should be re-evaluated and a non-drug treatment should be considered. If drug treatment is necessary, the lowest feasible dose of the drug should be used and alternative drugs with fewer adverse effects considered". In another example, Paula A Rochon, Jerry H Gurwitz, *The prescribing cascade revisited, Volume* 389, *ISSUE* 10081, P 1778-1780, May 6, 2017, states "Begin new medicines at low doses and tailor the dose to reduce the risk of adverse reactions. Consider the potential for any new symptoms to be caused by an adverse reaction, particularly if a medicine has been recently started or the dose changed. Ask patients if they have experienced any new symptoms, particularly if a medicine has been recently started or the dose changed. Provide patients with information about possible adverse effects of medicines and what to do when adverse drug reactions occur, e.g. in the form of Consumer Medicines Information. The decision to prescribe a second medicine to counteract an adverse drug reaction from a first medicine should only occur after careful consideration, and where the benefits of continuing therapy with the first medicine outweigh the risks of additional adverse reactions from the second medicine".

Using the method of deprescribing, which is the process of intentionally stopping a medication or reducing its dose to improve the person's health or reduce the risk of adverse drug reaction (ADR). This is usually relevant for people who take multiple medications for multiple conditions.

Clinical Decision Support Systems (CDSS) or point-of-care electronic alerts may be used to identify problematic drug combinations. It is noted that interactions due to drug combinations are a different problem. CDSS do not directly identify PC.

There are several drawbacks to existing approaches, for example:

Being manual, and relying on awareness by the physician and/or patients, which become impossible or at least extremely difficult for a human to perform even for a minimal number of medications due to the large number of possible combinations of medications, each one of which that may trigger an ADR. Moreover, such methods are subjective, being based on intuitive feelings of the physician, and therefore are prone to error. In contract, at least some systems, methods, apparatus, and/or code instructions described herein provide an objective, reproducible method.

The problem of identifying PC may be a complicated task that is too complex to identify (or solve) manually even for an experienced physician. Methods that rely on physician awareness when prescribing new medications and/or patient attention to new symptoms that may be related to newly prescribed drugs are limited in that when several drugs are taken in parallel, the number of possible combinations causing conflicts may be too large for a human to analyze. Manual methods are unable to cover all possible combinations and the joint effect of combinations of drugs.

As noted by Paula A Rochon, Jerry H Gurwitz, "Unfortunately, clinical decision support for drug prescribing most often focuses on the multiplicity of drug interactions, many of little consequence, but such decision support rarely targets prescribing cascades." PC basically relates to the prescription of drugs that treat symptoms caused by previously prescribed drugs. Even if there are no problematic drug interactions, an avoidable PC is not handled by current CDSS.

Even if a physician or a patient suspects the existence of a PC, they often do not have the appropriate tools to handle or solve it. In particular, when several drugs are involved, the number of combinations and drugs interdependencies becomes too large to manage manually.

In summary, standard practice solutions rely on doctors' and/or patients' awareness to the patient's conditions and ADR/symptoms and are mostly manual or semi-automatic. Such manual or semi-automatic systems are ineffective once the number of possible drug-symptom combinations become large. Existing CDSS handle problematic drug combinations which are different than PC.

It is noted that the systems, methods, apparatus, and/or code instructions described herein do not simply perform automation of a manual procedure. First, no manual equivalent of the process described herein has been previously described. The manual process of being aware of new symptoms and then looking at the prescribed medications to determine whether the new symptom is related to the prescribed medications is different than the automated process described herein. Second, the process described herein includes automated features which have no manual counterpart (i.e., cannot be performed manually by a human using pencil and/or paper). Inventors developed new steps that did not previously exist in the manual process, and do not have counterparts in the manual process, namely, computing a value indicative of risk of the new symptom being an adverse drug reaction (ADR) of one or a combination of the plurality of medications, for example, using a structured dataset optionally created from unstructured data. The computed value is reproducible, may be based on evidence, and/or may be accurate using data collected from multiple different sources.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
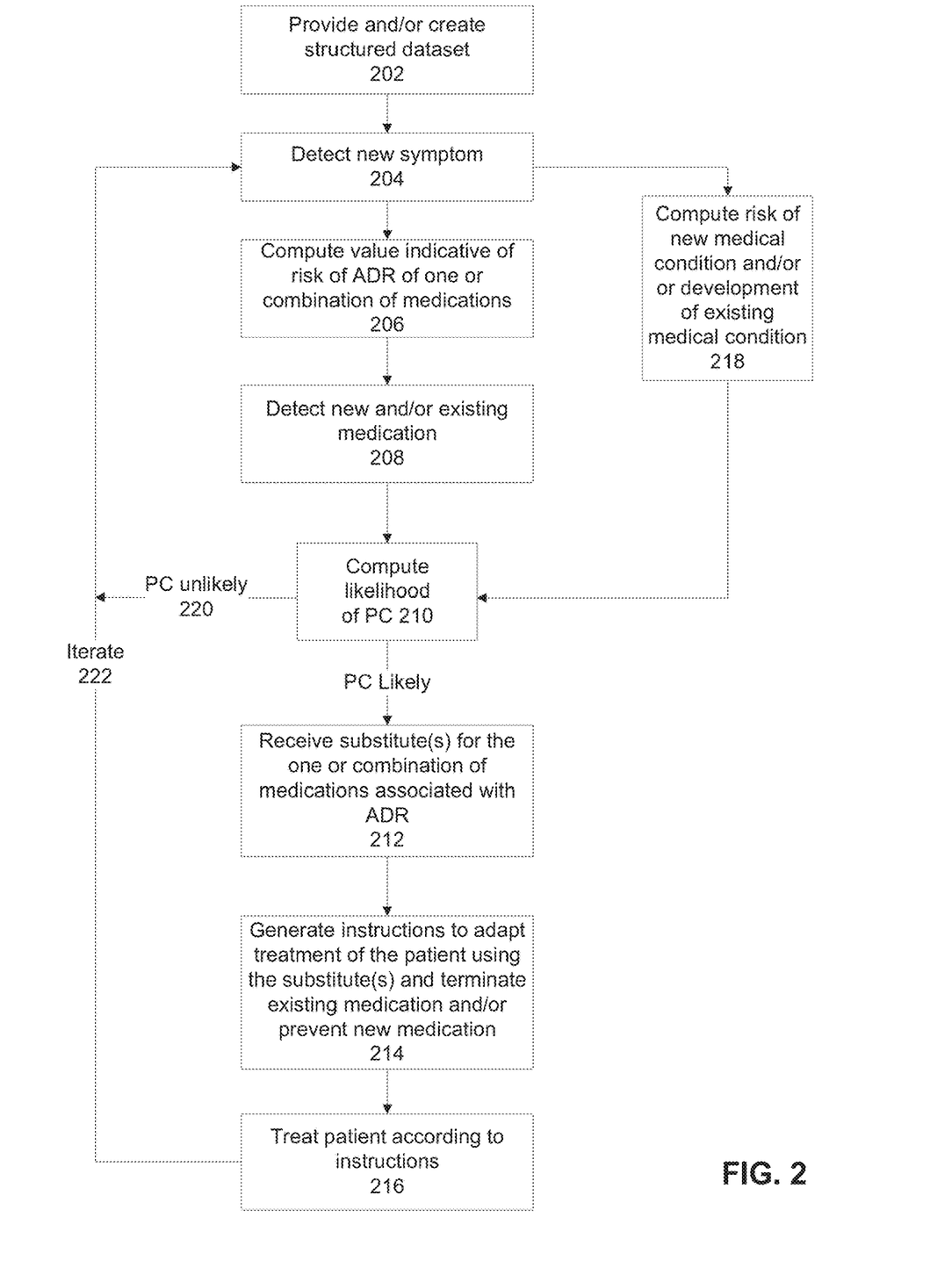
FIG. 2 is a flowchart of a method for generating instructions for adjusting a medical treatment of a patient for reducing likelihood of a prescription cascade, in accordance with some embodiments of the present invention.
Figure 3:
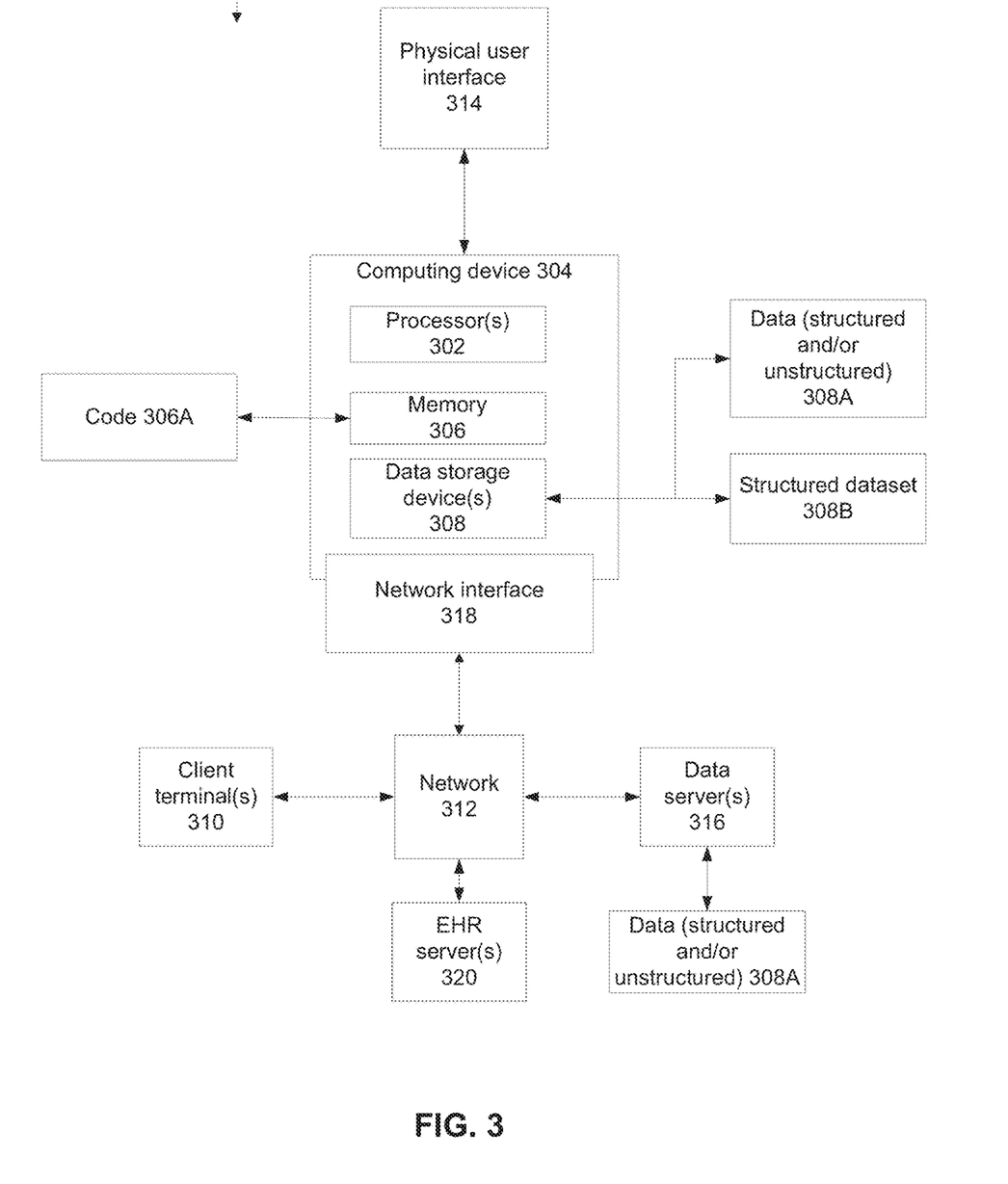
FIG. 3 is a block diagram of components of a system for adjusting a medical treatment of a patient for reducing likelihood of a prescription cascade, in accordance with some embodiments of the present invention.

Reference is now made to FIG. 2, which is a flowchart of a method for generating instructions for adjusting a medical treatment of a patient for reducing likelihood of a prescription cascade, in accordance with some embodiments of the present invention. Reference is also made to FIG. 3, which is a block diagram of components of a system 300 for adjusting a medical treatment of a patient for reducing likelihood of a prescription cascade, in accordance with some embodiments of the present invention. System 300 may implement the acts of the method described with reference to FIG. 2, by processor(s) 302 of a computing device 304 executing code instructions (e.g., code 306A) stored in a memory 306 (also referred to as a program store).

Computing device 304 may be implemented as, for example one or more and/or combination of: a group of connected devices, a client terminal, a server, a virtual server, a computing cloud, a virtual machine, an electronic health record server, an electronic prescription server, a desktop computer, a thin client, a network node, a network server, and/or a mobile device (e.g., a Smartphone, a Tablet computer, a laptop computer, a wearable computer, glasses computer, and a watch computer).

Different architectures of system 300 may be implemented, for example:

Computing device 304 may be implemented as one or more servers (e.g., network server, web server, a computing cloud, a virtual server, a network node, an EHR server, a prescription server) that provides services to multiple client terminals 310 over a network 312, for example, software as a service (SaaS), and/or other remote services.

Communication between client terminal(s) 310 and computing device 304 over network 112 may be implemented, for example, via an application programming interface (API), software development kit (SDK), functions and/or libraries and/or add-ons added to existing applications executing on client terminal(s), an application for download and execution on client terminal 310 that communicates with computing device 304, function and/or interface calls to code executed by computing device 304, a remote access section executing on a web site hosted by computing device 304 accessed via a web browser executing on client terminal (s) 310, client terminal(s) 310 may be implemented as thin clients and/or slaves and/or users of computing device 304.

For example, client terminals 310 may be implemented as code running on a tablet computer or smartphone used by a physician to prescribe medications to patients (e.g., while making rounds on patients on the ward, and/or by a family physician visiting patients at home) by connecting to computing device 304. In another example, client terminal(s) 310 may be implemented as a desktop PC in an office of a family physician that connects to computing device 304.

Computing device 304 may be implemented as a standalone device (e.g., client terminal, smartphone, server, computing cloud, virtual machine, kiosk) that includes locally stored code that implement one or more of the acts described with reference to FIG. 2. For example, computing device 304 may be implemented as a kiosk and/or desktop computer at a hospital used by physicians to prescribe medications to patients visiting the ER.

Hardware processor(s) 302 of computing device 304 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 302 may include a single processor, or multiple processors (homogenous or heterogeneous) arranged for parallel processing, as clusters and/or as one or more multi core processing devices.

Memory 306 stores code instructions executable by hardware processor(s) 302, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 306 stores code 306A that implements one or more features and/or acts of the method described with reference to FIG. 2 when executed by hardware processor(s) 302.

Computing device 304 may include data storage device(s) 308 for storing data, for example, data (e.g., structured and/or unstructured) 308A used for creating structured dataset 308B (as described herein). Data storage device(s) 308 may be implemented as, for example, a memory, a local hard-drive, virtual storage, a removable storage unit, an optical disk, a storage device, and/or as a remote server and/or computing cloud (e.g., accessed using a network connection).

Network 312 may be implemented as, for example, the internet, a local area network, a virtual network, a wireless network, a cellular network, a local bus, a point to point link (e.g., wired), and/or combinations of the aforementioned.

Computing device 304 may include a network interface 318 for connecting to network 312, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 304 and/or client terminal(s) 310 include and/or are in communication with one or more physical user interfaces 314 that include a mechanism for user interaction, for example, to enter data (e.g., enter a new prescription for a new medication) and/or to view data (e.g., view an alert indicative of PC).

Exemplary physical user interfaces 314 include, for example, one or more of, a touchscreen, a display, gesture activation devices, a keyboard, a mouse, and voice activated software using speakers and microphone.

Computing device 304 may communicate with one or more of the following over network 312:
Client terminal(s) 310, for example, used as endpoints where data is entered (e.g., new medication prescription) and/or where data is presented (e.g., alert indicating risk of PC, suggested substitute medications).
Data server(s) 316 storing data (structured and/or unstructured) 308A which is obtained and used to create structured dataset 308B.
EHR server(s) 320 storing EHR of patients, for example, used to detect currently prescribed medications and/or new symptoms and/or patient medical parameters, as described herein.

Client terminal(s) 310 and/or server(s) 316 and/or EHR server(s) 320 may be implemented as, for example, as a desktop computer, a server, a virtual server, a network server, a web server, a virtual machine, a thin client, and a mobile device.

Referring now back to FIG. 2, at 202, a structured dataset is provided and/or created. The structured dataset stores mappings between medications, symptoms, and medical conditions.

The structure dataset may be created from data extracted from one or more datasets, storing unstructured and/or structured data, for example, research publications, case reports, observational data, and pre-existing public databases.

The structure dataset may store extracted data according to population and/or sub-populations, for example, historical and existing patient medical conditions, age of onset of the medical condition(s), age of patient, gender, co-morbidities, and demographics, other medical history (e.g., smoking, recreational drug use, medications), and/or other patient parameters.

Storing data by patient population and/or sub-population may improve accuracy of the computation of the risk value for a target patient that correlates with a certain population and/or sub-population. Structured information may be extracted from unstructured data (e.g., from observational data), for example, using a causal inference process, for example, as described with reference to Hernán M A, Robins J M (2019). Causal Inference. Boca Raton: Chapman & Hall/CRC, forthcoming.

One or more of the following may be computed from relationships of the unstructured and/or structured data, and optionally stored in the structured dataset:

(i) A probability of a certain symptom to appear following treatment with one or a combination of certain medications. It is noted that some symptoms may appear due to a combination of two or more medications.

(ii) A probability that a certain symptom appears when one or a combination of certain medications are not being administered. For example, the symptom appears as a result of a new medical condition (e.g., disease) rather than as a side effect of medication.

(iii) One or a combination of certain drugs having documented evidence for treatment of a certain symptom.

(iv) One or more symptoms associated with a certain medical condition. For example, obtained from existing datasets such as Human Phenotype Ontology (HPO).

(v) One or a combination of certain drugs having documented evidence for treatment of a certain medical condition. For example, obtained from existing datasets such as NDF-RT, Drugbank.

Values for (i) and (ii) may be extracted and/or computed, at the (sub-) population level, from literature and/or knowledgebases (based, for example, on the age of onset of a given disease), and/or may be estimated for an individual patient (or sub-population) from observational data, for example, using the causal inference process.

In another example, retrospective longitudinal data (e.g., from electronic health records and/or other datasets) may be used to estimate and adjust the above described probabilities (i)-(v) (and to compute the corresponding confidence intervals), for example by using causal inference, to estimate the increase in probability of developing an ADR and/or symptom following certain medication administration compared to non-users (i.e., patients not administered the medication) control group. For example, causal inference and/or machine learning may be implemented for integrating the different data features and/or alert for potential PC as described herein. The one or more probabilities may be used in the decision making of whether there is a need for an alternative treatment for the given patient, as described herein.

The structured dataset may be dynamically updated, according to new data, for example, messages received from servers with the new data, and/or code that crawls a network (e.g., the internet) to servers storing data to check for new data.

Figure 4:
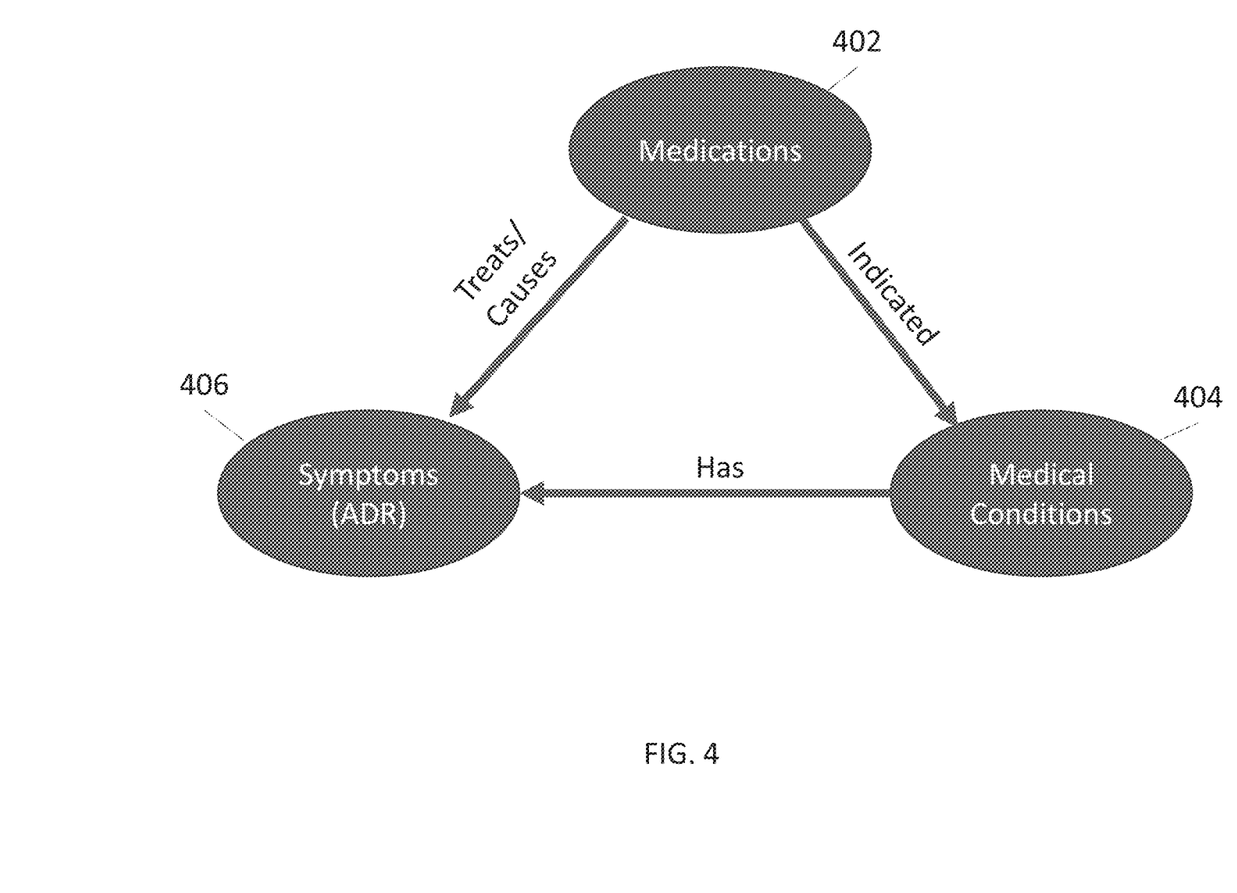
FIG. 4 is a schematic depicting mapping of data between medications, medical conditions, and symptoms stored in a structured dataset, in accordance with some embodiments of the present invention.

Reference is now made to FIG. 4, which is a schematic depicting mapping of data between medications 402, medical conditions 404, and symptoms 406 stored in a structured dataset, in accordance with some embodiments of the present invention. Medications 402 are mapped as indicated to medical conditions 404. Medications 402 are mapped as treating and/or causing symptoms 406, indicating an ADR. Medical conditions 404 are mapped as presenting with symptoms 406.

At 204, an indication of a new symptom appearing in a patient is detected.

The patient is treated with multiple medications for one or more medical conditions. For example, the number of medications used to treat the patient, is 2, 3, 4, 5, 6, 7, 8, 9, 10, or greater than 10. For example, the number of medical conditions the patient has been diagnosed with, is 2, 3, 4, 5, 6, 7, 8, 9, 10, or greater than 10.

The new symptom may be defined as a certain symptom that is temporally located (i.e., appears and/or is detected) after initial administration of one or combination of medications. The new symptom has not been present and/or has not been detected prior to the initial administration of one or combination of medications.

The indication of the new symptom may be detected by an analysis of an electronic health record (EHR) of the patient. The new symptom may be, for example, an entry in the EHR of the patient. For example, code may monitor the EHR of the patient to detect the indication of a new entry and/or value indicating the new symptom. Alternatively or additionally, the new symptom may be manually determined, for example, by the physician that examines the patient.

The new symptom may be defined according to a coding standard of symptoms.

At 206, a value indicative of risk (e.g., likelihood) of the new symptom being an adverse drug reaction (ADR) is computed. The ADR is likely due to one or a combination of the medications administered to the patient.

The value indicative of risk of the new symptom being ADR may be computed, for example, as the probability of the new symptom arising in the patient given that the patient suffers from medical condition(s) and given that one or a combination of medications have been administered to the patient. In terms of mathematical representation, value=P(Symptom|Medication(s), Medical condition(s) and/or other patient parameters).

The value indicative of risk of the new symptom being ADR may be represented as a probability value.

The value indicative of risk of the new symptom being an ADR may be computed according to data extracted from the structured dataset, at least storing mappings between medications and symptoms.

Optionally, the value indicative of risk of ADR is computed based on data of a population and/or sub-population of sample individuals correlated with medical parameters of the patient. Exemplary medical parameters include: historical and existing patient medical conditions, age of onset of the medical condition(s), age of patient, gender, co-morbidities, and demographics, other medical history (e.g., smoking, recreational drug use, medications), and/or other patient parameters. For example, for a 60 year old patient, who is a smoker, is obese, and has a history of type two diabetes, the value of risk is computed based on data obtained from other patients with similar ages that are smokers, are obese, and have type two diabetes. The data may be obtained from the structured dataset described herein.

At 208, an indication of a new and/or existing medication for treating the patient is detected. The new and/or existing medication is different than the one or combination of medications administered to the patient that are associated with risk of the new symptom ADR.

The new and/or existing medication is identified for treating the new symptom, as described herein.

The new medication is for future administration to the patient, i.e., at a time after occurrence (e.g., detection) of the new symptom. The existing medication may be currently administered to the patient, where the existing medication has been administered and/or instructed to be administered, to the patient after occurrence (e.g., detection) of the new symptom.

Optionally, the new medication is detected upon receiving instructions for administering the new medication, optionally prior to actual administration of the medication. For example, a user (e.g., physician) enters a prescription of the new medication into an electronic prescription system, and/or an indication of the new medication appears in the EHR of the patient.

Optionally, the exiting medication is detected by an analysis of the EHR and/or current prescriptions of the patient, as medications that are not for treatment of the medical condition, and as medications that have been ordered for the patient at a time after the time when the new symptom has been detected.

It is noted that 208 may be implemented in parallel, and/or before and/or after 206.

At 210, a likelihood of PC is computed. The likelihood of PC may be detected when the new and/or existing medication is identified for treating the new symptom, and when the value indicative of risk of ADR is according to a requirement.

The identification that the new and/or existing medication is for treating the new symptom may be determined, for example, based on an analysis of a dataset, optionally the structured dataset, that maps medications to the indication of the medication, i.e., what the medication is prescribed for treatment of.

Optionally, values indicative of risk that do not meet the requirement are indicative of a new medical condition, and/or progression of an existing medical condition, i.e., are not due to ADR.

The requirement may be, for example, a threshold value, and/or range of values, for example, a threshold probability value and/or range of probability values. For example, likelihood of ADR is detected when the value indicative of risk is greater than the threshold and/or greater than the range, for example, greater than 0.5, or greater than 0.6, or greater than 0.7, or greater than 0.8, or greater than 0.9, or greater than 0-0.5, or 0-0.6, or 0-0.7, or 0-0.8, or 0-0.9, or other values and/or ranges.

The requirement may be adjustable, for example, manually by the user, automatically by code, and/or computed according to desired target settings.

Alternatively or additionally, the requirement is based on comparing the value indicative of risk of ADR to a computed value indicative of likelihood of risk of the new symptom appearing when the one or combination of the medications are not administered, for example, computed as described with reference to act 218. The requirement may be, for example, that the value indicative of risk of the new symptom being ADR is greater than the computed value indicative of likelihood of risk of the new symptom appearing when the one or combination of medications are not administered. The term greater may be defined for example, as absolutely greater (i.e., >), statistically significantly greater, and/or greater by at least a defined probability value, for example, at least by about 0.1, or about 0.2, or about 0.3, or about 0.4, or about 0.5, or about 0.6, or about 0.7, or other smaller, greater, or intermediate values. For example, when the value indicative or risk of ADR=0.6, and the value indicative of likelihood of symptom appearing when no medication is administered=0.1, ADR is detected.

At 212, one or more substitute medications for the one or combination of the medications for treating the medical condition(s) of the patient are received when PC is computed as being likely. The one or more medications are associated with the new symptom ADR, as described herein. The substitute medication(s) is for treating the same medical condition that the one or combination of medications that are associated with ADR are treating, but is unlikely or less likely to cause the new symptom ADR.

The combination of medications has resulted in ADR in the form of the new symptom. A new medication is (or has already been) prescribed to treat the new symptom, which is actually ADR of other medications for treating the medical conditions, triggering the prescription cascade. Substitution of one or combination of medications for treating the medical condition is likely to prevent the prescription cascade, by removing the new symptom (i.e., ADR), which also removes the need for the new medication(s) for treating the ADR.

The substitute medications are selected for having low likelihood of triggering the detected new symptom (i.e., ADR), optionally for the target patient associated with one or more medication parameters, and which are likely to treat the medical condition of the patient.

Optionally, a request is generated for obtaining the substitute medication(s). The request may be for a manual selection of the substitute medication(s), and/or for an automated selection of the substitute medications. For example, the request may be a message presented on a display, requesting that a user selects a substitute medication for the medication(s) identified as causing the ADR. A list of substitute medications may be presented for selection by the user, for example, according to a dataset (e.g., the structured dataset) that maps medications to the medical conditions that are treated by the medications, and optionally maps the medications to symptoms which are ADR of the medications, in order to avoid or reduce risk of another ADR by the substitute medication. Alternatively or additionally, the request is for an automated selection of the substitute medication(s), optionally by code that analyzes the structured dataset. The code may automatically analyze the structured dataset for selecting the substitute medication according to a computed risk of developing the new symptom and/or other new symptoms in response to treatment of the medical condition with the substitute medication.

The substitute medications may be selected and/or presented in a ranked manner, for example, according to probability of resulting in new ADRs (e.g., computed according to parameters of the patient using the structured dataset), and/or according to effectiveness in treating the medical condition.

At 214, instructions for adjusting treatment of the patient by substituting the one or combination of the current medications with the substitute medication(s) may be generated. The instructions may include instructions for removing (e.g., terminating) the existing medication determined to be prescribed for treating the new symptom identified as ADR. Alternatively, the instructions avoid (e.g., do not include a) prescription of the new medication determined to be prescribed for treating the new symptom identified as ADR.

The instructions may be, for example, for manual substitution and/or automated substitution. For example, the instructions may be in the form of a recommendation for a new prescription for the patient based on the generated instructions for substitution of the medications. In another example, an electronic based prescription may be automatically generated according to the instructions for substitution of the medications. The instructions may be based on deprescribing protocols, for example, as described with reference to Ian A. Scott, Sarah N. Hilmer, Emily Reeve, BPharm et al, *Reducing Inappropriate Polypharmacy The Process of Deprescribing*, JAMA intern Med, 2015; 175(5): 827-834. doi:10.1001/jamainternmed.2015.0324.

At 216, the patient is treated for the medical condition by administration of the substitute medication(s), and optionally termination of the existing medication determined to be prescribed for treating the new symptom identified as ADR.

Referring now back to 204, 218 may be implemented in parallel (and/or sequentially with) 206. The output of 218 is provided to 210 for identifying likelihood of PC, as described herein. At 218, a computed value indicative of likelihood of the new symptom appearing when the one or combination of the medications are not administered. In other words, risk of the new symptom appearing in the patient as result of a new medical condition and/or a development of an existing medical condition, and not as an ADR of one or a combination of medications for treating medical condition(s). The value indicative of likelihood of risk of the new symptom appearing when the one or combination of the medications are not administered may be computed, for example, as the probability of the new symptom arising in the patient given that the patient suffers from medication condition(s) where the one or a combination of medications have not been administered to the patient. In terms of mathematical representation, value=P(Symptom| Medical condition(s) and/or other patient parameters).

The value indicative of likelihood of the new symptom appearing when the one or combination of the medications are not administered may be computed based on an analysis of data stored in the structured dataset.

The value indicative of likelihood of the new symptom appearing when the one or combination of the medications are not administered may be used in 210 for identifying likelihood of PC, as described herein.

At 220, the new and/or existing medication (detected in 208) being a PC is determined as being unlikely. That the new and/or existing medication is unlikely a PC is determined, for example, when the value indicative of likelihood of the new symptom appearing when the one or combination of the medications are not administered is according to a requirement, for example, above a probability threshold and/or range, for example, above about 0.9, or above about 0.8, or above about 0.7, or above about 0.6, or other smaller, larger, or intermediate values. In another example, PC is unlikely when the risk of ADR of one or combination of medications is statistically significantly lower than the value indicative of likelihood of the new symptom appearing when the one or combination of the medications are not administered.

At 222, one or more features described with reference to acts 204-220 are iterated. Optionally, the iterations are performed for a number of currently prescribed medications, for step-wise determining whether symptoms of the patient are due to ADRs, and iteratively removing medications causing the PC. Alternatively or additionally, the iterations are performed for monitoring the patient for new symptoms, and analyzing the new symptoms to determine whether they are due to ADR of medications for substitution to avoid or reduce likelihood of PC.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant medications will be developed and the scope of the term medication is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for generating instructions for adjusting a medical treatment of a patient for reducing likelihood of a prescription cascade (PC), comprising:

detecting an indication of a new symptom appearing in the patient being treated with a plurality of medications for at least one medical condition;

computing a value indicative of risk of the new symptom being an adverse drug reaction (ADR) of one or a combination of the plurality of medications based on a structured dataset automatically generated from unstructured data using a causal inference process, wherein the structured dataset is dynamically updated using new unstructured data or new structured data received from a plurality of servers;

detecting an indication of another new medication for treating the patient;

automatically generate a likelihood of PC in response to detecting that the new medication is for treating the new symptom and that the value indicative of the risk of the new symptom being the ADR is greater than a computed value indicative of likelihood of risk of the new symptom appearing with the one or combination of medications are not administered, wherein detecting that the new medication is for treating the new symptom comprises analyzing the structured dataset that maps medications to indications of the medications;

generating a request for at least one substitute medication for the one or combination of the plurality of medications in response to detecting the likelihood of PC; and generating instructions for adjusting treatment of the patient by substituting the one or combination of the plurality of medications with the at least one substitute medication, and for terminating administration of the new medication or avoiding administration of the new medication.

2. The method of claim 1, further comprising, in response to the request, automatically selecting at least one substitute medication according to a computed risk of developing the new symptom in response to treatment with the at least one substitute medication not being according to the requirement.

3. The method of claim 1, wherein the indication of the new symptom is detected by an analysis of an electronic health record (EHR) of the patient for determining when the new symptom temporally appears after administration of the one or combination of medications.

4. The method of claim 1, wherein likelihood of PC is generated in response to detecting that the value indicative of risk of the new symptom being the ADR of one or the combination of the plurality of medications is statistically significantly greater than the computed value indicative of likelihood of risk of the new symptom appearing when the one or combination of the plurality of medications are not administered.

5. The method of claim 1, wherein the patient is associated with a plurality of medical parameters, and the value indicative of risk is computed based on data of a population of a plurality of sample individuals correlated with the plurality of medical parameters.

6. The method of claim 5, wherein the plurality of medical parameters are selected from the group consisting of: historical and existing patient medical conditions, patient demographics, and age of onset of the existing patient medical conditions.

7. The method of claim 1, wherein the indication of the new medication is detected when the new medication comprises an existing medication currently being administered to the patient starting temporally after appearance of the new symptom.

8. The method of claim 7, wherein the indication of the new medication is detected when the new medication is instructed for future administration.

9. The method of claim 1, wherein values indicative of risk that do not meet the requirement are indicative of at least one of: a new medical condition, or progression of an existing medical condition.

10. The method of claim 1, wherein the value indicative of risk of the new symptom being an ADR is computed according to data extracted from the structured dataset storing mappings between medications, symptoms, and medical conditions.

11. The method of claim 10, further comprising: creating the structured dataset from data extracted from a plurality of datasets, by computing at least one member of the group consisting of: (i) a probability of a certain symptom to appear following treatment with one or a combination of certain medications, (ii) a probability that a certain symptom appears when one or a combination of certain medications are not being administered, (iii) one or a combination of certain drugs having documented evidence for treatment of a certain symptom, (iv) at least one symptom associated with a certain medical condition, (v) one or a combination of certain drugs having documented evidence for treatment of a certain medical condition.

12. The method of claim 11, further comprising, in response to the request, automatically analyzing the structured dataset for selecting at least one substitute medication according to a computed risk of developing the new symptom in response to treatment with at least one substitute medication not being according to the requirement.

13. The method of claim 11, wherein the plurality of datasets include unstructured data including research publications and case reports.

14. The method of claim 1, wherein the new symptom is defined according to a coding standard of symptoms.

15. The method of claim 1, further comprising generating a recommendation for an electronic based prescription for the patient based on the generated instructions, wherein the one or combination of the plurality of medications are substituted with at least one substitute medication and wherein the recommendation includes instructions to at least one of terminate and avoid administration of the new medication.

16. The method of claim 1, wherein a number of the plurality of medications is at least 5.

17. A system for generating instructions for adjusting a medical treatment of a patient for reducing likelihood of a prescription cascade (PC), comprising:

at least one hardware processor executing a code for:
detecting an indication of a new symptom appearing in the patient being treated with a plurality of medications for at least one medical condition;

computing a value indicative of risk of the new symptom being an adverse drug reaction (ADR) of one or a combination of the plurality of medications based on a structured dataset automatically generated from unstructured data using a causal inference process, wherein the structured dataset is dynamically updated using new unstructured data or new structured data received from a plurality of servers;

detecting an indication of another new medication for treating the patient;

automatically generating a likelihood of PC in response to detecting that the new medication is for treating the new symptom and that the value indicative of the risk of the new symptom being the ADR is greater than a computed value indicative of likelihood of risk of the new symptom appearing with the one or combination of medications are not administered;

generating a request for at least one substitute medication for the one or combination of the plurality of medications in response to detecting the likelihood of PC, wherein detecting that the new medication is for treating the new symptom comprises analyzing the structured dataset that maps medications to indications of the medications; and generating instructions for adjusting treatment of the patient by substituting the one or combination of the plurality of medications with the at least one substitute medication, and for terminating administration of the new medication or avoiding administration of the new medication.

18. A computer program product for generating instructions for adjusting a medical treatment of a patient for reducing likelihood of a prescription cascade (PC), comprising:

a non-transitory memory storing thereon code for execution by at least one hardware process, the code including instructions for:

detecting an indication of a new symptom appearing in the patient being treated with a plurality of medications for at least one medical condition;

computing a value indicative of risk of the new symptom being an adverse drug reaction (ADR) of one or a combination of the plurality of medications based on a structured dataset automatically generated from unstructured data using a causal inference process, wherein the structured dataset is dynamically updated using new unstructured data or new structured data received from a plurality of servers;

detecting an indication of another new medication for treating the patient;

computing automatically generating a likelihood of PC in response to detecting that the new medication is for treating the new symptom and that the value indicative of the risk of the new symptom being the ADR is greater than a computed value indicative of likelihood of risk of the new symptom appearing with the one or combination of medications are not administered, wherein detecting that the new medication is for treating the new symptom comprises analyzing the structured dataset that maps medications to indications of the medications;

generating a request for at least one substitute medication for the one or combination of the plurality of medications in response to detecting the likelihood of PC; and generating instructions for adjusting treatment of the patient by substituting the one or combination of the plurality of medications with the at least one substitute medication, and for terminating administration of the new medication or avoiding administration of the new medication.

19. The computer program product of claim 18, comprising code including instructions for crawling a network to servers storing data to check for the new unstructured data or new structured data.

20. The method of claim 1, comprising, iteratively:

detecting additional new symptoms, computing values indicative of risk of the additional new symptoms being adverse drug reactions (ADRs), detecting indications of new medications for treating the patient, generating additional likelihoods of PC, and generating requests for additional substitute medications for the one or combination of the plurality of medications in response to detecting the likelihood of PC.

* * * * *